United States Patent [19]

Sportelli et al.

[11] Patent Number: 4,707,846
[45] Date of Patent: Nov. 17, 1987

[54] FULL SPINE SHIELDING MEANS

[76] Inventors: Louis Sportelli, 175 Delaware Ave., Palmerton, Pa. 18071; James F. Winterstein, 167 Hedge Ct., Glen Ellyn, Ill. 60137

[21] Appl. No.: 743,797
[22] Filed: Jun. 12, 1985
[51] Int. Cl.[4] ............................................. G21K 1/00
[52] U.S. Cl. .................................... 378/145; 378/147
[58] Field of Search ...................... 378/145, 147–148, 378/150

[56] References Cited

U.S. PATENT DOCUMENTS

| 2,426,884 | 9/1947  | Kieffer.             |         |
|-----------|---------|----------------------|---------|
| 2,925,496 | 2/1960  | Zoubek.              |         |
| 3,114,043 | 12/1963 | Thomas et al.        |         |
| 3,233,248 | 2/1966  | Bushnell.            |         |
| 3,631,249 | 12/1971 | Friede.              |         |
| 3,649,835 | 3/1972  | Brackenbrough et al. |         |
| 3,678,233 | 7/1972  | Faw et al.           |         |
| 3,937,971 | 2/1976  | Morrison et al.      |         |
| 3,944,838 | 3/1976  | Gäde.                |         |
| 3,950,651 | 4/1976  | Flocée.              |         |
| 4,082,957 | 4/1978  | Morlan.              |         |
| 4,163,902 | 8/1979  | Musaph.              |         |
| 4,214,167 | 7/1980  | Gäde.                |         |
| 4,221,971 | 9/1980  | Burger               | 378/148 |
| 4,266,139 | 5/1981  | Sportelli et al.     |         |
| 4,352,987 | 10/1982 | Hayashi et al.       |         |
| 4,472,637 | 9/1984  | Sportelli et al.     |         |
| 4,472,828 | 9/1984  | Ferlic               | 378/147 |
| 4,476,569 | 10/1984 | Ogo                  | 378/147 X |

FOREIGN PATENT DOCUMENTS 1402202  5/1965  France.
 187933 10/1966  U.S.S.R..

Primary Examiner—Frederick R. Schmidt
Assistant Examiner—Judy J. Hartman
Attorney, Agent, or Firm—Sanford J. Piltch

[57] ABSTRACT

A shielding or masking device for use in conjunction with an X-ray radiation generating source comprised of radiopaque material having a vertically oriented opening having a broader portion twice the width of the upper, narrower portion nearer its distal or lower end to block entirely or confine radiation dosage to a specific area of a subject under observation or inspection and to prevent unnecessary and excessive radiation dosages to the subject during full spine radiographs.

10 Claims, 4 Drawing Figures

FULL SPINE SHIELDING MEANS

BACKGROUND OF THE INVENTION

It is known in the art that in order to provide shielding or filtration in association with radiation sources masking or shielding devices are required. Such shielding devices take on various configurations depending on the method of providing the shield, the size of the area to be shielded and the type of radiation source. Various radiation shielding configurations have been developed in connection with X-ray radiography to provide against the excessive exposure of the subject to radiation.

It is also known in rhe art that filtration or diffusion of radiation provides against excessive exposure of the subject. Various devices have been developed to filter the radiation generated in connection with X-ray radiography. All of these devices need to be mounted in close association to the source of the radiation in order to provide maximum shielding against, or filtration of, the radiation.

The prior developments of the inventors of the present invention are exemplary of the devices known in the art and teach the use of both a shielding means and a filtration means for providing either shield or a filter for the radiation generated in connection with X-ray radiography. These prior developments also teach the use of a specialized mounting means to cooperatively place the shield or filter in close association to the source of the radiation to provide maximum benefit to the subject in permitting the least amount of excessive exposure to unnecessary radiation. These developments are described in U.S. Pat. Nos. 4,266,139 and 4,472,637 and typify the present state of the art in this field.

It is an object of the present invention to carry these developments one step further and to provide a masking device to block all radiation from the radiation source not needed to cause an image to appear on an X-ray film for the specific area of the subject to be observed or inspected.

It is a further object of the present invention to provide a masking device which cooperates with the earlier developed shielding and filtering devices and the standard X-ray systems in use today.

It is also an object of the present invention to provide a masking device which is compact, easy to use, versatile and resilient to continued use and not quickly subject to irradiation from an X-ray radiation generating source.

SUMMARY OF THE INVENTION

The masking device of the present invention relates generally to radiation shielding devices and more particularly to X-ray shielding devices having a shielding means to block entirely or confine radiation dosage to specific areas of a subject. Specifically, the present invention provides a shielding or masking means to confine or direct the X-ray radiation to a specific area under observation or inspection and to prevent unnecessary and excessive radiation dosages to the subject during full spine radiographs.

The full spine shielding means is comprised of a metallic shield or mask constructed of lead or other radiopaque material, said shield being provided with a vertically oriented elongated slot or opening having a broader portion nearer its distal or lower end for permitting only the X-ray radiation necessary to cause an image to appear on the X-ray film for the specific area to be observed or inspected, the spinal column and the pelvic region, to pass through the slot or opening and for blocking the unnecessary radiation from contacting the subject and causing excessive exposure to such radiation. Said shield is laminated between two pieces of translucent plastic or other suitable material and is configured for positioning in close association with an X-ray radiation generating source, for example, on the front of the collimator of an X-ray machine.

In the preferred embodiment of the present invention, the shield is located immediately adjacent to and in front of the collimator of an X-ray machine in cooperation with a mounting means having two sets of transverse tracks, one set for receiving and securing the shield of the present invention and the second set for receiving and adjustably securing a substantially rectangular transparent plate, wherein the transparent plate may be frictionally secured to the mounting means and, thus, to the X-ray radiation generating source. Other shielding means or filtering means may be adjustably positioned on the transparent plate to actively cooperate with the shield of the present invention in preventing excessive radiation to reach specific areas of the subject under observation or inspection.

BRIEF DESCRIPTION OF THE DRAWINGS

For the purposes of illustrating the invention, there are shown in the drawings forms which are presently preferred; it being understood, hoewver, that the invention is not limited to the precise arrangements and instrumentalities shown.

DETAILED DESCRIPTION OF THE INVENTION

The following detailed description is of the best presently contemplated modes of carrying out the present invention. This description is not intended in a limiting sense but is made solely for the purpose of illustrating the general principles of the invention.

Figures 1, 4:
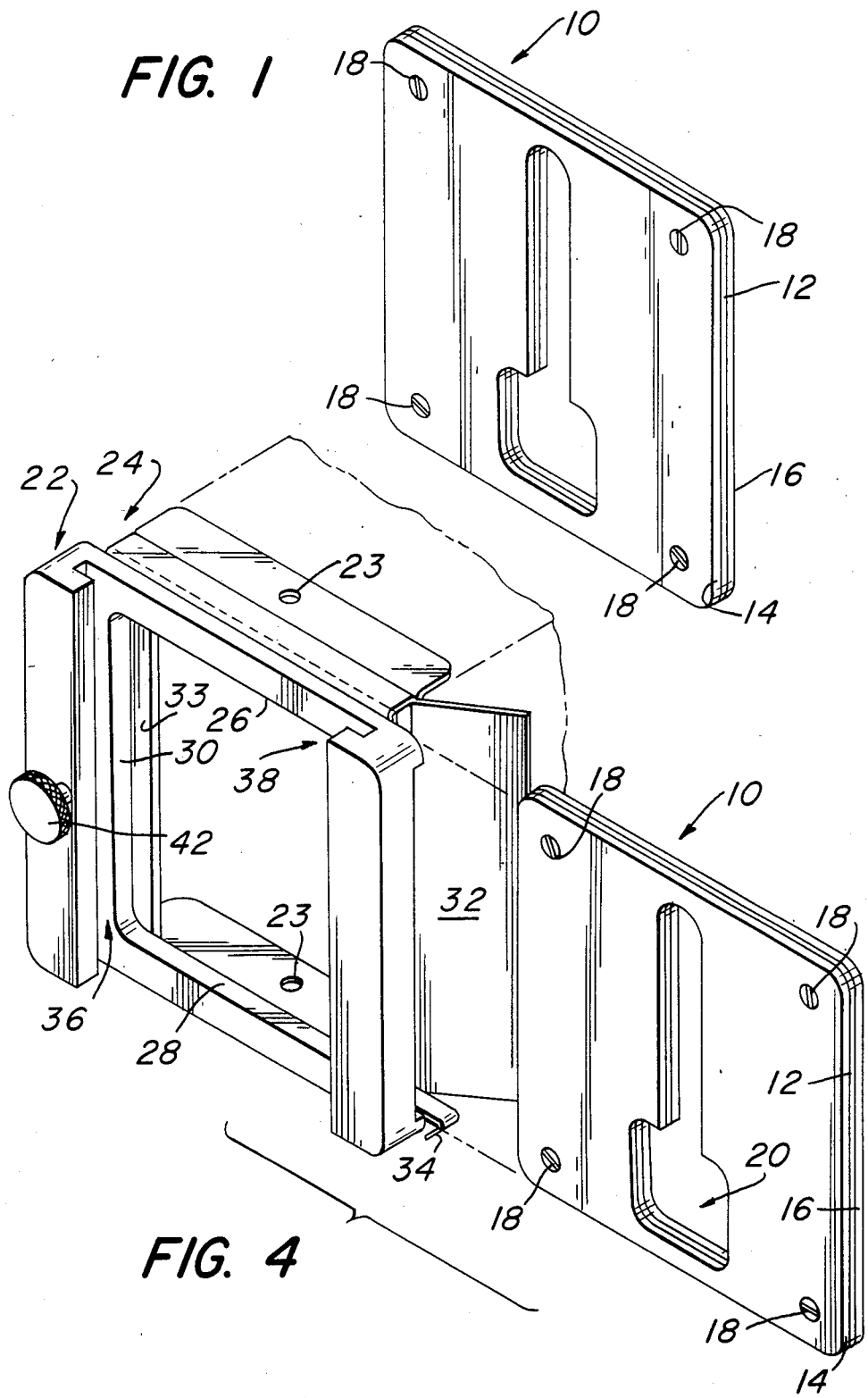
FIG. 1 is an isometric view of the shielding or masking means of the present invention showing the separate layers and the opening or slot.
FIG. 4 is a partially exploded isometric view of the shielding or masking means of the present invention showing the guide and clamp means of the mounting means.

Referring now to the drawings in detail, wherein like numerals indicate like elements, there is shown in FIG. 1 the shielding or masking means of the present invention designated generally as 10. The shielding means 10 is substantially square in configuration but may be rectangular or otherwise shaped so as to provide for the blocking of all radiation unnecessary in the creating of an image on an X-ray film of the area under observation or inspection. The shielding means 10 is preferred to be substantially square in shape and approximately 5 inches along a side so as to cooperatively mount immediately adjacent to and in front of the collimator of existing X-ray machinery.

The shielding means 10 is comprised of a metallic plate 12 consisting of lead or other suitable material of sufficient thickness to block X-ray radiation. The metallic plate 12 is laminated between two similarly shaped plates of translucent plastic 14, 16 or other suitable material which will not suffer degradation when subjected to intense and repeated exposures to radiation. The thickness of the translucent plastic plates 14, 16 is dependent upon the radiation degradation factor. It is recommended, however, that the plates 14, 16 be at least 0.125 inches thick to withstand normal use in this environment. The plates 12, 14 and 16 may be secured one to the other by means of threadable screws 18 or other suitable means. It is preferred that the threadable screws 18 are inserted through plate 14, then through plate 12 and threaded into previously threaded holes in plate 16 to securely fasten the plates one to the other.

The plates, 12, 14 and 16 are provided with an elongated opening or slot 20 vertically positioned medially along the horizontal measurement of the shielding means 10. A broader or widened portion of the slot 20 is located at the lower or distal end of the slot. This widened portion is approximately twice the width of the upper, narrower portion of the slot 20 and comprises the bottom fourth or one-quarter portion of the slot. The slot 20 provides for the free passage of X-ray radiation from an X-ray radiation generating source to the particular subject area. The remaining portion of the shielding means 10 effectively blocks all other radiation emanating from the X-ray radiation generating source which is not required to form an image on an X-ray film of the area under observation or inspection so as to prevent the subject from exposure to unnecessary and excessive radiation.

Referring to FIG. 4, the shielding means 10 is provided with a mounting means 22 adapted to be placed and maintained in front of an X-ray radiation discharge opening of an X-ray machine, for example, a collimator (shown in dotted lines). The mounting means 22 may be permanently secured to the X-ray machine through the holes 23 provided in the top and bottom flanges of the mounting bracket 24 which supports the mounting means. The mounting means 22 is attached to the support bracket 24 by an upper and a lower horizontally placed track which securely hold the cooperating surfaces of and the mounting means in a fixed position and prevent it from moving laterally or outwardly away from the collimator. The lateral positioning is maintained by an abutment wall along the distal side of the bracket 24 and a spring and release tab (34) at the track entrance, both elements being well known in the mechanical arts and similar to the abutment wall and spring and release tab described later in connection with the mounting of the shielding means 10.

The shielding means 10 is placed in the mounting means 22 by slidably moving it into the tracks 26, 28 and up against the abutment wall 30. This placement is facilitated by a guide means placed at an angle to the tracks 26, 28 so that the shielding means 10 more easily aligns with the tracks. The shielding means 10 is only loosely held in place by the tracks 26, 28 and rests against a retaining means 33 vertically oriented along the wall 30 to keep the shielding means 10 substantially aligned with the mounting means 22. To retain the lateral positioning of the shielding means 10 a spring member (not shown) is used which operates in conjunction with the spring and release tab 34.

The mounting means 22 also includes a second set of tracks 36, 38 which are positioned at an angle of 90 degrees to the first set of tracks 26, 28 so that a transparent cover plate 40 may slide into the tracks 36, 38. The cover plate 40 is fixedly secured in the tracks 36, 38 by a threaded fastener 42. Looking now at FIG. 2, the cover plate 40, also of a preferred substantially rectangular or square configuration, is shown secured in place by the fastener 42 between the tracks 36, 38. The cover plate 40 may be constructed of plastic or other appropriate material suitable for the use and environment. In its preferred embodiment the transparent cover plate 40 is provided with a rectangular slot medially disposed along its horizontal measurement to avoid interference with the X-ray radiation emissions passing through the elongated opening 20 of the shielding means 10. The cover plate 40 will preferably also be provided with one or two annular openings or finger holes 44, 46 to facilitate manual placement and removal of the plate. The cover plate 40 also functions to retain the shielding means 10 in substantial juxtaposed alignment with the collimator as the X-ray machine may be moved or tilted for specific positioning.

Alternatively, the shielding means 10 may be placed inside the mounting means 22 within the opening formed by the tracks 26, 28 and the wall 30. The cover plate 40 is then inserted to hold the shielding means 10 in position in front of the collimator.

Figure 2:
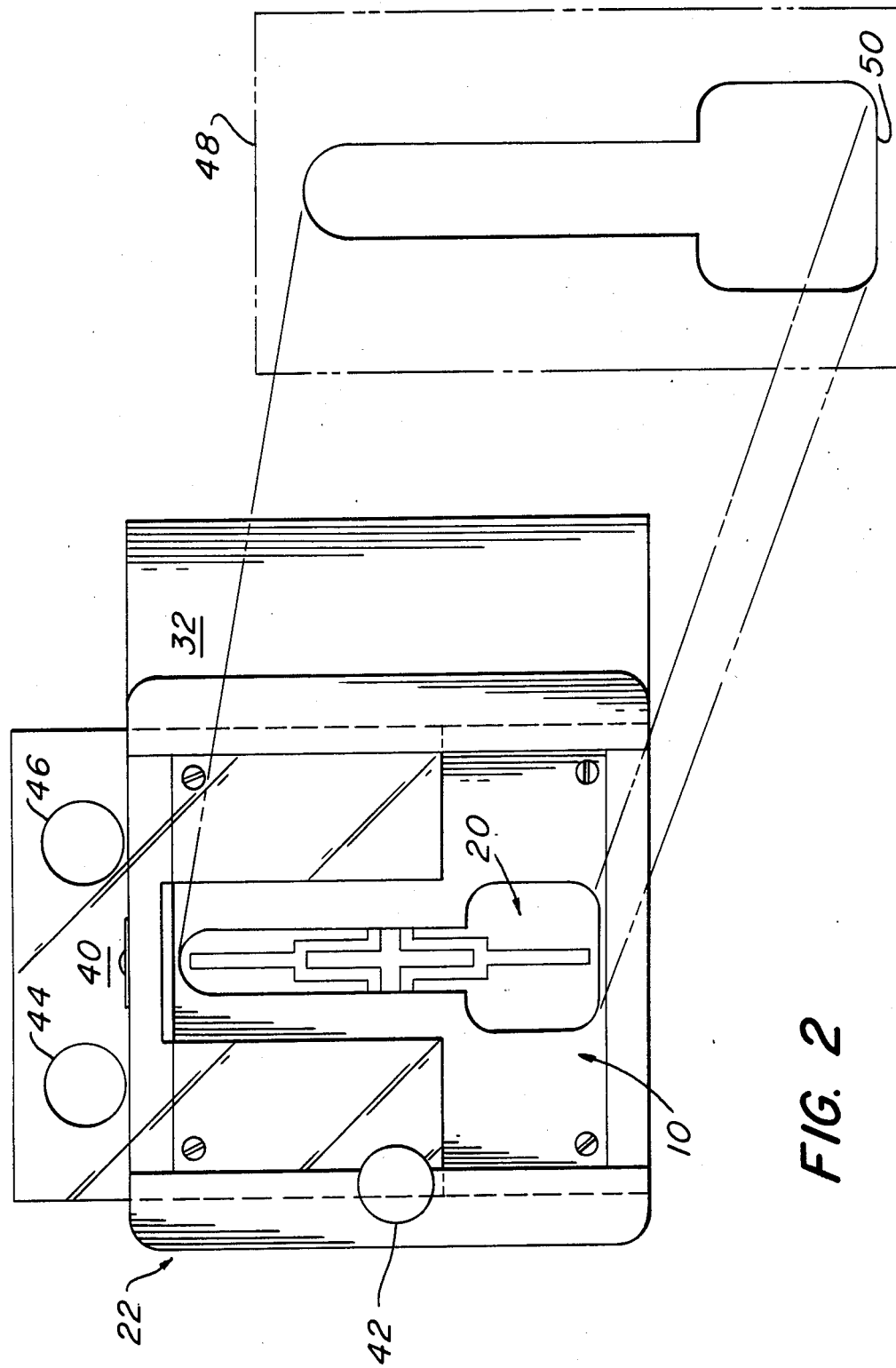
FIG. 2 is a front plan view of the shielding or masking means of the present invention showing the transparent plate and showing the image of the radiation permitted to pass through the shielding means as it strikes an X-ray film.

FIG. 2 demonstrates the operation of the full spine shielding means of the present invention. The shielding means 10 is placed in the mounting means 22 immediately adjacent and in front of the X-ray machine collimator, shown in the center background of the drawing as the bisecting openings in the X-ray screen. As can be readily observed from the drawing, the shielding means 10 blocks all X-ray radiation emitted from the collimator field except for the radiation which freely passes through the elongated slot 20 of the shielding means. The image created by the passed X-ray radiation is shown on the X-ray film 48 displaying the image 50 of the elongated slot 20 of the shielding means 10. In its desired application, such shielding or masking will result in exposure of the entire spine but limited to a narrow area along either side of the cervical, dorsal and lumbar regions. The narrow strip widens at the bottom, as does the elongated slot 20, to encompass the entire pelvic region. Such shielding or masking significantly reduces excessive exposure of the human body, or the particular subject area of the body to be observed or inspected, to X-ray radiation.

Figure 3:
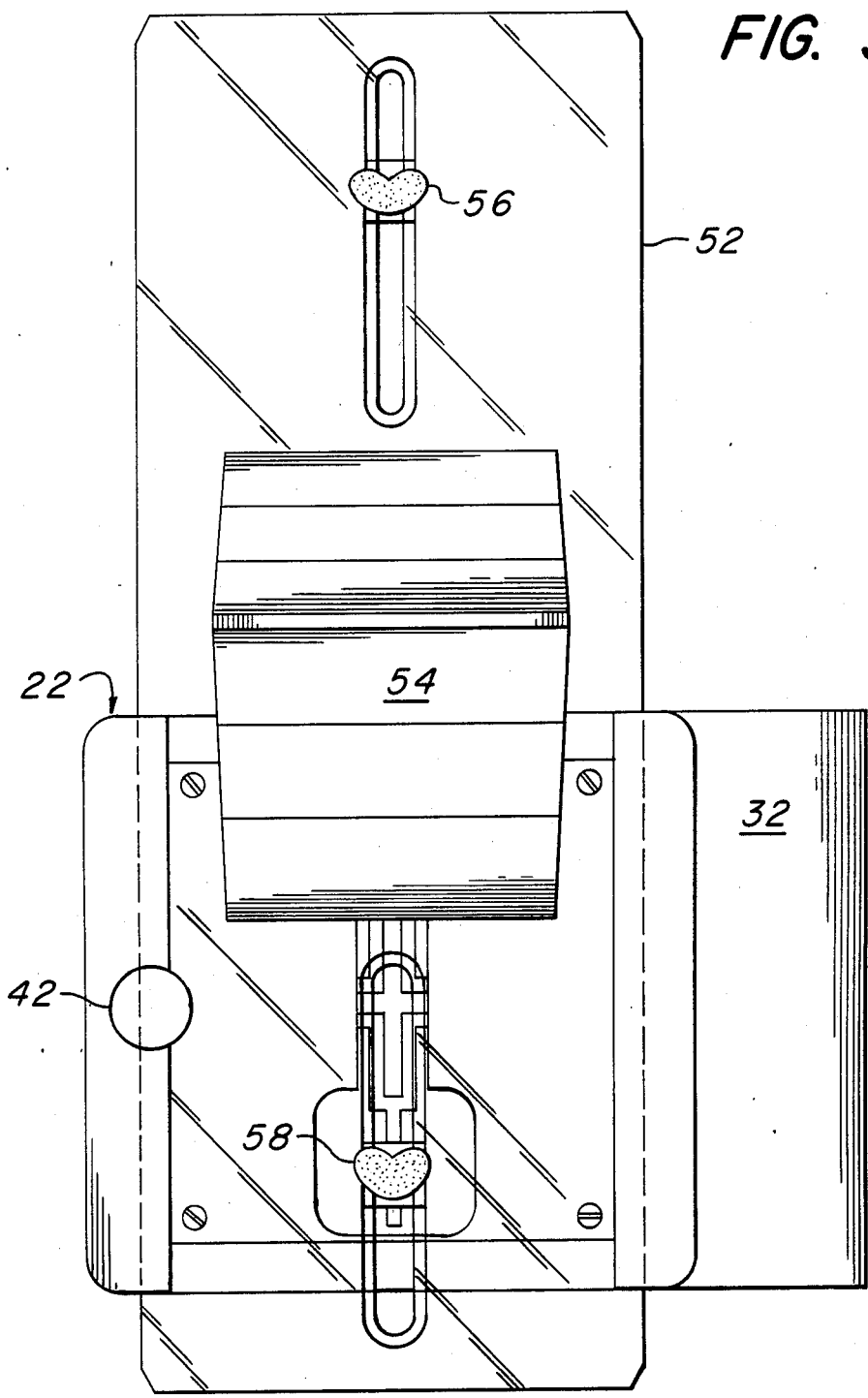
FIG. 3 is a front plan view of the shielding or masking means of the present invention showing a different transparent plate having other shielding means and filtering means disposed thereon.

FIG. 3 shows the shielding means 10 in conjunction with additional shielding and filtering means. The transparent plate 52 including a wedge-type X-ray filtering means 54 and reproductive gland shielding means 56, 58 can be used with the shielding means 10 of the present invention to provide greater protection from excessive X-ray radiation primarily in the pelvic region. The plate 52, similarly to cover plate 40, is positioned and secured using the tracks 36, 38 and the fastener 42 as described above. The plate 52 also functions to retain the shielding means 10 in substantial juxtaposed alignment with the collimator of the X-ray machine as it is fixedly secured in tracks 36, 38 by threaded fastener 42 in similar fashion and arrangement as is cover plate 40. Reference may be had to U.S. Pat. Nos. 4,266,139 and 4,472,637 for detailed descriptions of the wedge-type filtering means 54 and the gland shielding means 56, 58 referred to herein other than the present invention producing structural relationships in accordance with the invention. The gland shielding means, when positioned in front of the widened portion of the elongated slot 20 of the shielding means 10 will reduce the effective radiation to the pelvic region in the area of the reproductive glands so as not to expose that particular area of the body to excessive radiation.

Thus the present invention is capable of effectively reducing the exposure of particular areas of the human body to excessive unnecessary radiation from an X-ray radiation generating source. This is accomplished by confining the necessary radiation to a particular area and blocking all other radiation from contact with the subject. The radiation necessary to create an image on an X-ray film will pass through the opening in the shielding or masking means while all other radiation is substantially blocked by the shield. The resultant X-ray will be exposed only in the areas coextensive with the elongated slot of the shielding or masking means. Additionally, if a gland shield is used, the area coextensive with that shield will also remain unexposed as the glandular area has been effectively protected from the X-ray radiation by blocking such radiation with the shield. A significant step in reducing unnecessary exposure to X-ray radiation will be accomplished with use of the present invention.

The present invention may be embodied in other specific forms without departing from the spirit or essential attributes thereof and, accordingly, reference should be made to the claims rather than to the specification as indicating the scope of the invention.

We claim:

1. A masking means for directing radiated energy to a specific area of a subject under observation or inspection comprising a first radiation shielding or filtering means having a vertically oriented elongated opening with a broader portion nearer its distal or lower end, said opening located medially along the horizontal, positioned immediately adjacent to and in front of the collimator of an X-ray radiation generating device within a space in a mount or support means defined by two sets of transverse tracks, a first set of tracks for removably positioning said first shielding or filtering means in said space and a second set of tracks transverse to said first set of tracks capable of removably securing and adjustably positioning a second shielding or filtering means adjustably secured to a substantially rectangular transparent plate, said transparent plate being juxtaposed in front of and against said first shielding or filtering means for retaining said first shielding or filtering means within its defined space and in juxtaposition to the collimator, said second shielding or filtering means being positioned to actively cooperate with said first shielding or filtering means for permitting only the X-ray radiation necessary to cause an image to appear on the X-ray film for the specific area to be observed or inspected to pass through to be filtered by said first and second shielding or filtering means and for blocking unecessary radiation from contacting the subject and causing excessive exposure to such radiation.

2. The masking means of claim 1 wherein said first radiation shielding or filtering means is substantially rectangular in configuration and comprised of a metallic radiopaque plate laminated between two similarly configured plates of translucent plastic.

3. The masking means of claim 1 wherein the broader portion of said elongated opening being in the lower one-fourth of said opening.

4. The masking means of claim 1 wherein the broader portion of said elongated opening being twice the width of the upper, narrower portion.

5. A full spine shielding means for directing radiated energy to a specific area of a subject under observation or inspection comprising a first radiation shielding or filtering means having a vertically oriented elongated opening with a broader portion nearer its distal or lower end, said opening located medially along the horizontal with said broader portion being in the lower one-fourth of said opening and twice the width of the upper, narrower portion, positioned immediately adjacent to and in front of the collimator of an X-ray radiation generating device within a space in a mount or support means defined by two sets of transverse tracks, a first set of tracks for removably positioning said first shielding or filtering means in said space and a second set of tracks transverse to said first set of tracks capable of removably securing and adustably positioning a second shielding or filtering means adjustably secured to a substantially rectangular transparent plate, said transparent plate being juxtaposed in front of and against said first shielding or filtering means for retaining said first shielding or filtering means within its defined space and in juxtaposition to the collimator, said second shielding or filtering means being positioned to actively cooperate with said first shielding or filtering means for permitting only the X-ray radiation necessary to cause an image to appear on the X-ray film for the specific area to be observed or inspected to pass through or be filtered by said first and second shielding or filtering means and for blocking unecessary radiation from contacting the subject and causing excessive exposure to such radiation.

6. The full spine shielding means of claim 5 wherein said first radiation shielding or filtering means is substantially rectangular in configuration and comprised of a metallic radiopaque plate laminated between two similarly configured plates of translucent plastic.

7. A masking means for directing radiated energy from an X-ray radiation generating source to a specific area of a subject under observation or inspection including a means for attaching a support means to a front portion of a collimator of an X-ray radiation generating machine, said support means having first and second sets of transverse tracks, said second set of tracks capable of removably securing and adjustably positioning a radiation shielding or filtering means adjustably secured to a substantially rectangular transparent plate within said second set of tracks, the improvement comprising another radiation shielding or filtering means having a vertically oriented elongated opening with a broader portion nearer its distal or lower end, said opening being located medially along the horizontal, removably interposed in juxtaposition between the collimator of the X-ray radiation generating machine and said transparent plate within a space defined by said first set of tracks of said support means and being retained in said juxtaposition within said support means by said transparent plate, said another radiation shielding or filtering means being positioned to actively cooperate with said radiation shielding or filtering means for permitting only the X-ray radiation necessary to cause an image to appear on the X-ray film for the specific area to be observed or inspected to pass through or be filtered by said shielding or filtering means and for blocking unnecessary radiation from contacting the subject and causing excessive exposure to such radiation.

8. The masking means of claim 7 wherein said another radiation shielding or filtering means is substantially rectangular in configuration and comprised of a metallic radiopaque plate laminated between two similarly configured plates of translucent plastic.

9. The masking means of claim 7 wherein the broader portion of said elongated opening being in the lower one-fourth of said opening.

10. The masking means of claim 7 wherein the broader portion of said elongated opening being twice the width of the upper, narrower portion.

* * * * *